United States Patent
Rudnik et al.

(10) Patent No.: US 12,066,423 B2
(45) Date of Patent: Aug. 20, 2024

(54) SYNTHETIC TARGET MATERIAL FOR SHAPED CHARGE PERFORMANCE EVALUATION, POWDERED METAL

(71) Applicant: Hunting Titan, Inc., Pampa, TX (US)

(72) Inventors: Ian Douglas Rudnik, Vassar, MI (US); Christopher Brian Sokolove, Midlothian, TX (US); Laura Montoya Ashton, Ithaca, NY (US); Morgan Tompkins, Tijeras, NM (US)

(73) Assignee: Hunting Titan, Inc., Pampa, TX (US)

( * ) Notice: Subject to any disclaimer, the term of this patent is extended or adjusted under 35 U.S.C. 154(b) by 823 days.

(21) Appl. No.: 17/156,388

(22) Filed: Jan. 22, 2021

(65) Prior Publication Data

US 2021/0164958 A1    Jun. 3, 2021

Related U.S. Application Data

(60) Division of application No. 16/386,028, filed on Apr. 16, 2019, now abandoned, which is a continuation of application No. 15/506,195, filed as application No. PCT/US2015/047581 on Aug. 28, 2015, now Pat. No. 10,309,952.

(Continued)

(51) Int. Cl.
| | |
|---|---|
| *G01N 33/22* | (2006.01) |
| *E21B 43/117* | (2006.01) |
| *E21B 43/119* | (2006.01) |
| *F41J 1/08* | (2006.01) |
| *F42B 1/02* | (2006.01) |
| *F42B 35/00* | (2006.01) |
| *G01N 3/08* | (2006.01) |
| *G01N 3/40* | (2006.01) |

(52) U.S. Cl.
CPC .......... *G01N 33/227* (2013.01); *E21B 43/117* (2013.01); *E21B 43/119* (2013.01); *F41J 1/08* (2013.01); *F42B 35/00* (2013.01); *G01N 3/08* (2013.01); *G01N 3/40* (2013.01); *F42B 1/02* (2013.01)

(58) Field of Classification Search
CPC .......... G01N 3/40; G01N 3/08; G01N 33/227; E21B 43/117; E21B 43/119; F42B 1/02; F42B 35/00; F41J 1/08; F41J 1/01
See application file for complete search history.

(56) References Cited

U.S. PATENT DOCUMENTS

| | | |
|---|---|---|
| 2,582,719 A | 1/1952 | Ramsey |
| 4,932,239 A | 6/1990 | Regalbuto |

(Continued)

FOREIGN PATENT DOCUMENTS

| | | |
|---|---|---|
| EP | 1243890 A1 | 9/2002 |
| WO | 2014123510 A1 | 8/2014 |

OTHER PUBLICATIONS

Notification of Transmittal of the International Search Report and the Written Opinion of the International Searching Authority, PCT Application No. PCT/US2015/47581, mailed Jan. 20, 2016, 11 pages.

(Continued)

*Primary Examiner* — Paul M. West

(57) ABSTRACT

A shaped charge target apparatus and method for using a target composed of synthetic material, thereby allowing for repeatable testing at a variety of density and hardness values.

5 Claims, 4 Drawing Sheets

Related U.S. Application Data

(60) Provisional application No. 62/043,072, filed on Aug. 28, 2014.

(56) References Cited

U.S. PATENT DOCUMENTS

| | | | |
|---|---|---|---|
| 6,238,595 | B1 | 5/2001 | Brooks et al. |
| 6,505,559 | B1 | 1/2003 | Joslin et al. |
| 7,146,913 | B2 | 12/2006 | Bell |
| 7,160,379 | B1 | 1/2007 | Shoshany et al. |
| 10,309,952 | B2 | 6/2019 | Rudnik et al. |
| 2005/0189141 | A1* | 9/2005 | Bell .................. E21B 29/02 175/4.6 |
| 2009/0217739 | A1 | 9/2009 | Hardesty et al. |
| 2009/0241700 | A1 | 10/2009 | Haggerty et al. |
| 2009/0308662 | A1 | 12/2009 | Lyons |

OTHER PUBLICATIONS

Communication pursuant to Rule 164(1) EPC and partial supplementary European search report based on European application No. 15834890.4, mailed Feb. 16, 2018, 15 pages.

Rook, Melvin et al.(Jan. 1, 2009). Perforator Performance Study Determines Optimum System and Achieves Field Performance Projections. Society of Petroleum Engineers. Retrieved from the Internet: URL:https://www.onepetro.org/conference-paper/SPE-124343-MS?sort=&start=B&q="api+rp+19b"+OR+11 api+I9b 11&from year=&peer reviewed=&published between=&fromSearchResults=true&to year=&rows=I0# [retrieved on Feb. 7, 2018].

Author: unknown, Title: Recommended Practices for Evaluation of Well Perforators, Date: Sep. 28, 2001, Publisher: American Petroleum Institute, pp. 41.

Author: Welsh, B.S, Title: High speed deformation and breakup of shaped charge jets, PhD thesis, Date: 1993, Publisher: University of Nottingham, pp. 222.

Author: unknown, Title: The New Encyclopaedia Britannica, Date: 1982, Publisher: Encyclopedia Britannica, Inc., Edition: 15th, Pertinent Pages: cover, bibliographic, p. 620, p. 621, p. 1065, p. 1074.

L. 0. Asuquo et al: "Characteristics of Zircon Sand and the Effect on Foundry Casting", Journal of Mechanics & Industry Research, vol. 1, No. 1, Jun. 5, 2013 (Jun. 5, 2013), pp. 27-32, XP055572774, DOI: 10.12966/jmir.05.06.2013.

Dupont: "DuPont(TM) Zircore /Kyasill(TM) foundry sand", 2006, pp. 1-4, XP55572758,EPO Form 2906 01 .91TRI USA Retrieved from the Internet: URL:https://www.chemours.com/Titanium_Technologies/es_US/products/zircore_kyasil/MI_B_H_69478_3.pdf [retrieved on Mar. 21, 2019).

Simchi A: "The role of particle size on the laser sintering of iron powder", Metallurgical and Materials Transactions B, Springer-Verlag, New York, vol. 35, No. 5, Oct. 1, 2004 (Oct. 1, 2004), pp. 937-948, XP019697647, ISSN: 1543-1916.

Communication and supplementary European search report based on European application No. 15834890.4, mailed Jun. 5, 2018, 12 pages.

Office action mailed Oct. 7, 2020, U.S. Appl. No. 16/386,028, 7 pages.

Office action mailed Dec. 22, 2020, U.S. Appl. No. 16/386,028, 16 pages.

* cited by examiner

SYNTHETIC TARGET MATERIAL FOR SHAPED CHARGE PERFORMANCE EVALUATION, POWDERED METAL

RELATED APPLICATIONS

This application is a divisional application of U.S. Non-provisional application Ser. No. 16/386,028 filed Apr. 16, 2019, which is a continuation of U.S. Non-provisional application Ser. No. 15/506,195 filed Feb. 23, 2017, which is a 371 of International Application No. PCT/US15/47581, filed Aug. 28, 2015, which claims priority to U.S. Provisional Application No. 62/043,072, filed Aug. 28, 2014.

FIELD

The invention generally relates to methods and apparatus for testing shaped charges. More particularly, the invention relates to the use of shape charge targets composed of synthetic materials.

BACKGROUND OF THE INVENTION

Generally, when completing a subterranean well for the production of fluids, minerals, or gases from underground reservoirs, several types of tubulars are placed downhole as part of the drilling, exploration, and completions process. These tubulars can include casing, tubing, pipes, liners, and devices conveyed downhole by tubulars of various types. Each well is unique, so combinations of different tubulars may be lowered into a well for a multitude of purposes.

A subsurface or subterranean well transits one or more formations. The formation is a body of rock or strata that contains one or more compositions. The formation is treated as a continuous body. Hydrocarbon deposits may exist within the formation. Typically a wellbore is drilled from a surface location, placing a hole into a formation of interest. Completion equipment is placed downhole after drilling, including casing, tubing, and other downhole equipment as needed. Perforating the casing and the formation with a perforating gun is a well known method in the art for accessing hydrocarbon deposits within a formation from a wellbore.

Explosively perforating the formation using a shaped charge is a widely known method for completing an oil well. A shaped charge is a term of art for a device that when detonated generates a focused explosive output. This is achieved in part by the geometry of the explosive in conjunction with an adjacent liner. Generally, a shaped charge includes a metal case that contains an explosive material with a concave shape and has a thin metal liner on the inner surface of the explosive material. Many materials are used for the liner including brass, copper, tungsten, and lead. When the explosive detonates the liner metal is compressed into a super-heated, super pressurized jet that can penetrate metal, concrete, and rock.

A perforating gun has a gun body. The gun body typically is composed of metal and is cylindrical in shape. Within a typical gun tube is a charge holder or carrier tube, which is a tube that is designed to hold the actual shaped charges. The charge holder contains cutouts called charge holes where the shaped charges are placed.

A shaped charge is typically detonated by a booster or igniter. Shaped charges may be detonated by electrical igniters, pressure activated igniters, or detonating cord. One way to ignite several shaped charges is to connect a common detonating cord that is placed proximate to the igniter of each shaped charge. The detonating cord is comprised of material that explodes upon ignition. The energy of the exploding detonating cord can ignite shaped charges that are properly placed proximate to the detonating cord. Often a series of shaped charges may be daisy chained together using detonating cord.

Shaped charges are tested to ensure quality control as well as determine performance characteristics. A common test is to place a shaped charge on top of a plate and concrete cylinder. A steel jacket may surround the concrete cylinder. The test setup is typically located in a bunker for safety reasons. The shaped charge is then detonated remotely from a control station. The concrete cylinder is then opened up to determine the depth of the penetration as well as the deviation of the hole from the center of the cylinder. One problem with this method is that the concrete is always curing and is therefore not shelf stable for long periods of time. A further problem with concrete targets is that its properties (such as compressive strength and density) in general are difficult to control, resulting in inconsistent test data. Concrete is also too soft to gauge shaped charge performance in hard rock applications.

Natural rock targets are also commonly used for testing for improved accuracy of down hole charge performance. Berea sandstone is one of the most common natural rock targets. These rock targets are generally expensive. Moreover, availability of specific examples is sometimes limited. Rock targets also require complicated confinement designs to simulate the natural stresses in oil and gas producing formations.

Solid steel targets are used for targets. One problem with a steel target is that it is non-porous. An explosive jet passing through a porous medium versus a non-porous one may exhibit significant differences. This results in test data that is not always applicable to the field. Also, steel has a high compressive strength that makes it not suitable for simulating medium or soft formations.

Aluminum targets are also used to test shaped charges. Aluminum has the same problem as steel in that it is non-porous. Another problem with aluminum is that it may react with the materials in the high explosive jet. These reactions may result in disruption of the jet and erratic penetration patterns. Both of these problems result in inconsistent test data that does not always apply to field conditions.

SUMMARY OF EXAMPLES OF THE INVENTION

An example of the invention may include a shaped charge target puck comprising a powdered material, wherein the powder is pressed into a cylindrical shape and then sintered. A variation of the example may include the powdered material comprising powdered iron, powdered carbon, powdered copper, or powdered molybdenum, or any combination of the identified materials. A variation of the example may include the target comprising a density of approximately 3.34 g/cc with a hardness of approximately 61.1 HRP, approximately 4.35 g/cc with a hardness of approximately 70.3 HRP, approximately 4.69 g/cc with a hardness of approximately 75.4 HRP, or approximately 5.34 g/cc with a hardness of approximately 92.2 HRP. A variation of the example may include the target comprising a density range of 2.7 g/cc to 8 g/cc. A variation of the example may include the target comprising a hardness range of 48.8593 HRP to 128.1844 HRP.

Another example of the invention may include a method for testing a shaped charge comprising pressing a powdered material into a disc, sintering the disc, placing the disc proximate to a shaped charge, and firing the shaped charge into the disc. A variation of the example may include the disc being between 1 and 4 inches diameter. The example may further comprise placing a metal plate between the shaped charge and the disc. The example may further comprise hardness testing the disc. The example may further comprise stacking one or more discs underneath the first disc to form a plurality of discs. The example may further comprise placing the plurality discs in a test fixture. The example may further comprise saturating the plurality of discs with a fluid. The example may further comprise applying a compressive radial stress to the plurality of discs. The example may further comprise applying a compressive axial stress to the plurality of discs. A variation of the example may include the powdered material including a powdered wax component that is burned off during the sintering process. A variation of the example may include the powdered material including lubricating additives that burns off during the sintering process.

Another example of the invention may include a shaped charge test apparatus comprising a first end cap adapted to accept a shaped charge, a second end cap, and a body containing a hollow cylindrical interior adapted for accepting a plurality of synthetic target discs. The example may further comprise a first reservoir within the body adapted to contain a first fluid. The example may further comprise a second reservoir within the first end cap adapted to contain a second fluid. The example may further comprise synthetic target discs being composed of sintered powdered material. The example may include the powdered material being composed of a metallic powder. The example may further include the second end cap having a through opening. The example may further include a shape charge being oriented to fire through the second fluid and the plurality of synthetic target discs.

Another example of the invention may include a shaped charge test apparatus comprising a cylindrical fixture with a hollow portion adapted for accepting a plurality of synthetic target cylinders about its outer surface, and having a hallow annulus adapted to accept a perforating gun. A variation of the example may include the plurality of synthetic target cylinders located perpendicular to the outer surface of the cylindrical fixture. A variation of the example may include each synthetic target cylinder further comprises a plurality of synthetic targets stacked inside. Furthermore, each synthetic target may comprise a powdered material, wherein the powder is pressed into a cylindrical shape and then sintered. A variation of the example may include the powdered material comprising powdered iron, powdered carbon, powdered copper, or powdered molybdenum, or any combination of the identified materials. A variation of the example may include the powdered material comprising a density of approximately 3.34 g/cc with a hardness of approximately 61.1 HRP, approximately 4.35 g/cc with a hardness of approximately 70.3 HRP, approximately 4.69 g/cc with a hardness of approximately 75.4 HRP, or approximately 5.34 g/cc with a hardness of approximately 92.2 HRP. A variation of the example may include the powdered material comprising a density range of 2.7 g/cc to 8 g/cc. A variation of the example may include the powdered material comprising a hardness range of 48.8593 HRP to 128.1844 HRP.

DESCRIPTION OF THE DRAWINGS

For a thorough understanding of the present invention, reference is made to the following detailed description of the preferred embodiments, taken in conjunction with the accompanying drawings in which reference numbers designate like or similar elements throughout the several figures. Briefly.

DETAILED DESCRIPTION OF EXAMPLES OF THE INVENTION

In the following description, certain terms have been used for brevity, clarity, and examples. No unnecessary limitations are implied and such terms are used for descriptive purposes only and are intended to be broadly construed. The different apparatus and method steps described herein may be used alone or in combination with other systems and method steps. It is to be expected that various equivalents, alternatives, and modifications are possible within the scope of the appended claims.

Figure 1:
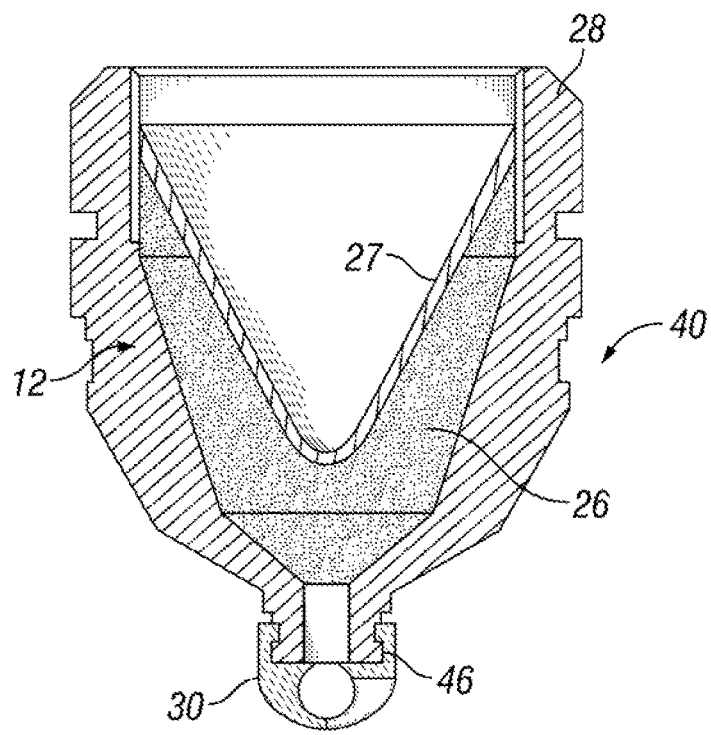
FIG. 1 is a shaped charge.

Referring to an example shown in FIG. 1, a shaped charge 12 includes a shaped charge case 28 that holds the energetic material 26 and the liner 27. The shaped charge case 28 typically is composed of a high strength metal, such as alloy steel. The liner 27 is usually composed of a powdered metal that is either pressed or stamped into place. The metals used in liner 27 may include brass, copper, tungsten, and lead. The retainer fitting 30 is secured to the end fitting 46 of the shaped charge case 28 by snapping into place over a flange on end fitting 46. The entire assembly 40 includes shaped charge 12 combined with retainer fitting 30. Alternatively, the fitting 30 could be threaded onto the charge case 18, secured with adhesive, snapped around the full length of the charge case, or formed integrally with the charge case. The fitting 30 could also be secured to the charge case 18 using set screws, roll pins, or any other mechanical attachment mechanisms. Alternatively, shaped charge case 28 could be integrally formed to retaining fitting 30. This would result in a single component, thus reducing cost and complexity.

Figure 2A:
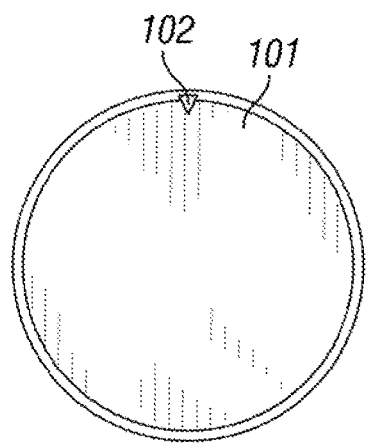
FIGS. 2A, 2B, and 2C are different views of a synthetic target.
Figure 2B:
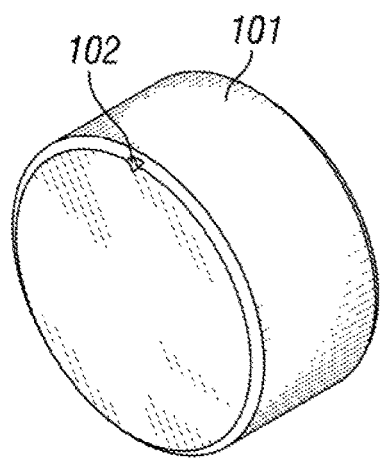
Figure 2C:
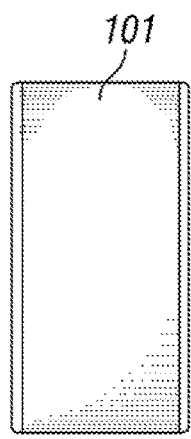

An example synthetic target is shown in FIGS. 2A, 2B, and 2C. The synthetic target 101 in this example is approximately two inches in diameter and one inch in depth. The depth and the diameter may vary. Other dimensions may include a four inch diameter disc with a two inch depth. The synthetic target 101 can be composed of metal powder. The synthetic target 101 may be composed of a combination of metal and ceramic powders. The powder used could include one or more of the elements iron, carbon, copper, and molybdenum. The powder is pressed into the shape of a disk. The pressed synthetic target 101 is then sintered in an inert atmosphere. Afterwards it may be allowed to furnace cool. The indicator 102 designates the top surface of the synthetic target 101 for testing and quality control purposes. The side pressed down on, in this case the top surface with the indicator 102, may exhibit a different hardness value than the bottom surface. In this example the synthetic target 101 is shaped as a disk or puck, however it may be shaped in any number of configurations, including rectangular, square, oval, or any other configuration necessary.

An example of a powder mix for the synthetic target 101 may include North American Hoganas R 12 Fe with 10% RXM 100 Cu powder plus 1.5% Mo (−325 mesh), +1.5% graphite, and Asbury 1651+0.75% Acrawax X atomized lubricant powder. Wax and lubricating additives can be used in the powder mix. Common examples of lubricating additives include carbon or graphite. The wax and lubricating additives make the powder metal easier to process. Furthermore, during the sintering process the wax and lubricating additives burn off and create voids in the synthetic target 101. These voids give the synthetic target 101 its low density and high porosity if that is desired. The range of likely densities sought for the synthetic targets is between 2.7 and 8.0 g/cc. The potential hardness values associated with that range of density is from 40 to 150 HRP.

An important advantage of synthetic targets over concrete is that they are shelf stable. Synthetic targets can be stored for long periods of time without changing their performance. However, concrete continues to cure, thus making it stronger and harder with time.

An advantage of using synthetic targets is that it the density and hardness are easily changed in order to accommodate specific testing requirements. For example, a pressed density of 3.5 g/cc may result in a sintered density of 3.56 g/cc and a Brinell hardness of 23.3 HB 10/500. Another example may include a pressed density of 4.4 g/cc, resulting in a sintered density of 4.34 g/cc and a Brinell hardness of 43.2 HB 10/500. Another example may include a pressed density of 5.0 g/cc, resulting in a sintered density of 4.84 g/cc and a Brinell hardness of 56.7 HB 10/500. Another example may include a pressed density of 5.6 g/cc, resulting in a sintered density of 5.4 g/cc and a Brinell hardness of 71.8 HB 10/500. These examples provide the ability to evaluate shaped charge performance across a broad range of formation stresses and naturally occurring rocks with differing properties.

In some applications Rockwell Hardness P (HRP) is a better measurement of hardness for synthetic targets. In at least one example, a measured density of 3.34 g/cc corresponds to an average measured hardness of approximately 61.1 HRP. In at least another example, a measured density of 4.35 g/cc corresponds to an average measured hardness of approximately 70.3 HRP. In at least another example, a measured density of 4.69 g/cc corresponds to an average measured hardness of approximately 75.4 HRP. In at least another example, a measured density of 5.34 g/cc corresponds to an average measured hardness of approximately 92.2 HRP. In another example the density may range from 2.7 g/cc to 8 g/cc, corresponding to a range of hardness of approximately 48.8593 HRP to 128.1844 HRP.

Figure 3:
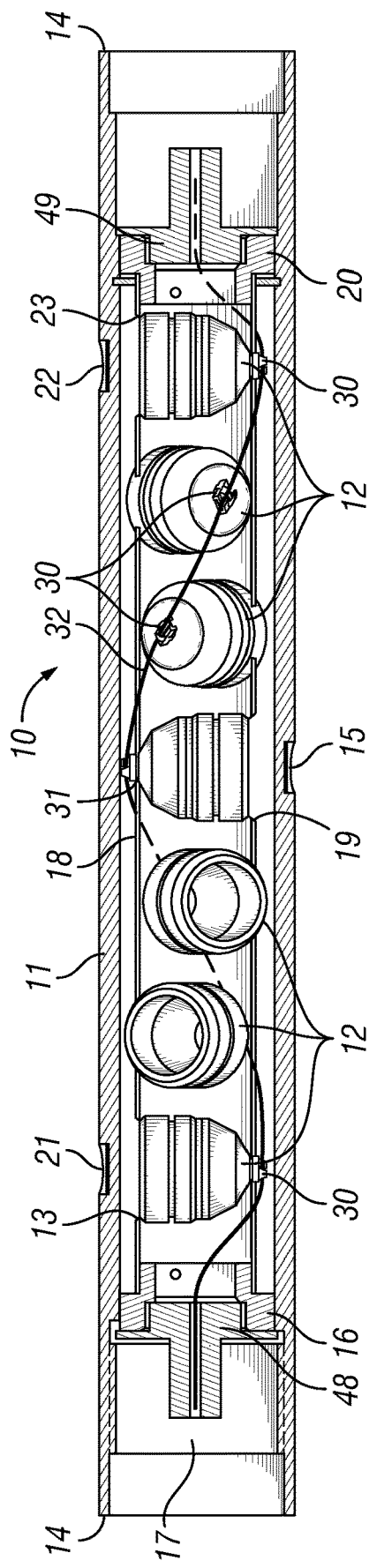
FIG. 3 is a cross section of a perforating gun.

Referring to an example shown in FIG. 3, a typical perforating gun 10 comprises a gun body 11 that houses the shaped charges 12. The gun body 11 contains end fittings 16 and 20 which secure the charge holder 18 into place. The charge holder 18 in this example is a charge tube and has charge holes 23 that are openings where shaped charges 12 may be placed. The charge holder 18 has retainer cutouts 31 that are adapted to fit a retainer fitting 30 in a predetermined orientation. The gun body 11 has threaded ends 14 that allow it to be connected to a series of perforating guns 10 or to other downhole equipment depending on the job requirements. In this example the retainer fitting 30 is separate from the charge holder 18, however in another variation of the embodiment that retainer fittings 30 may be integral to the charge holder 18. Each shaped charge 12 has an associated retainer fitting 30 that secures each shaped charge 12 to the charge holder 18 and the detonating cord 32. The detonating cord 32 runs the majority of the length of the gun body 11 beginning at end cap 48 and ending at end cap 49. The detonating cord 32 wraps around the charge holder 18 as shown to accommodate the different orientations of the shaped charges 12. In this embodiment, the shaped charges 12 have an orientation that is rotated 60 degrees about the center axis of the gun body 11 from one shaped charge to the next. Other orientations may include a zero angle, where all of the shaped charges 12 are lined up. Other orientations may have different angles between each shaped charge 12. This example using a 60 degree phase is illustrative and not intended to be limiting in this regard.

Figure 4:
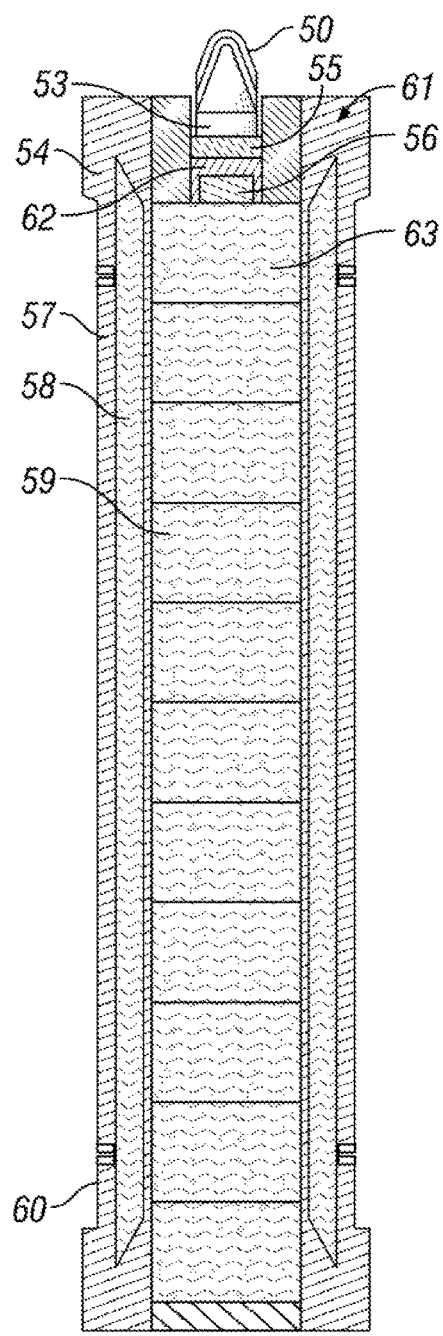
FIG. 4 is shaped charge test setup.

Referring to FIG. 4, a shaped charge 50 is tested with a test fixture 61 to simulate perforating in downhole conditions. In this test setup the shaped charge 50 may be secured to a piece of casing 53, simulating the perforating gun casing that is penetrated during the perforating event. A fluid barrier 55 is created wherein a void in the test fixture 61 is filled with a fluid. This simulates the fluid existing in the annulus between the perforating gun and the downhole casing. In this case the fluid may include water, drilling mud, or other fluids or combinations of fluids of interest that may be found downhole. A metallic barrier 62 simulates the casing. A concrete barrier 56 simulates the presence of concrete between the casing and the formation. The formation material 59 is comprised of one of more cylindrical synthetic target segments 63. These segments may be the same hardness or a variety of hardness values to simulate different formations. The formation material 59 may be sealed and filled with a fluid to saturate the synthetic target segments 63. The fluid used to saturate the formation material 59 may include water, mineral spirits, paint thinner, or some other fluid or combinations of fluids.

The test fixture 61 contains a body 57, a top cap 54, and a bottom cap 60. The bottom cap 60 may have an opening to atmosphere or it may be sealed with a base plate. The base plate may have a hole that may include threads or some other mechanism for adapting the hole to a fitting. The test fixture 61 may include a fluid space 58 that wraps around the test fixture in 360 degrees. The fluid space 58 may be pressurized in order to apply a radial pressure against the formation material 59.

Figure 5:
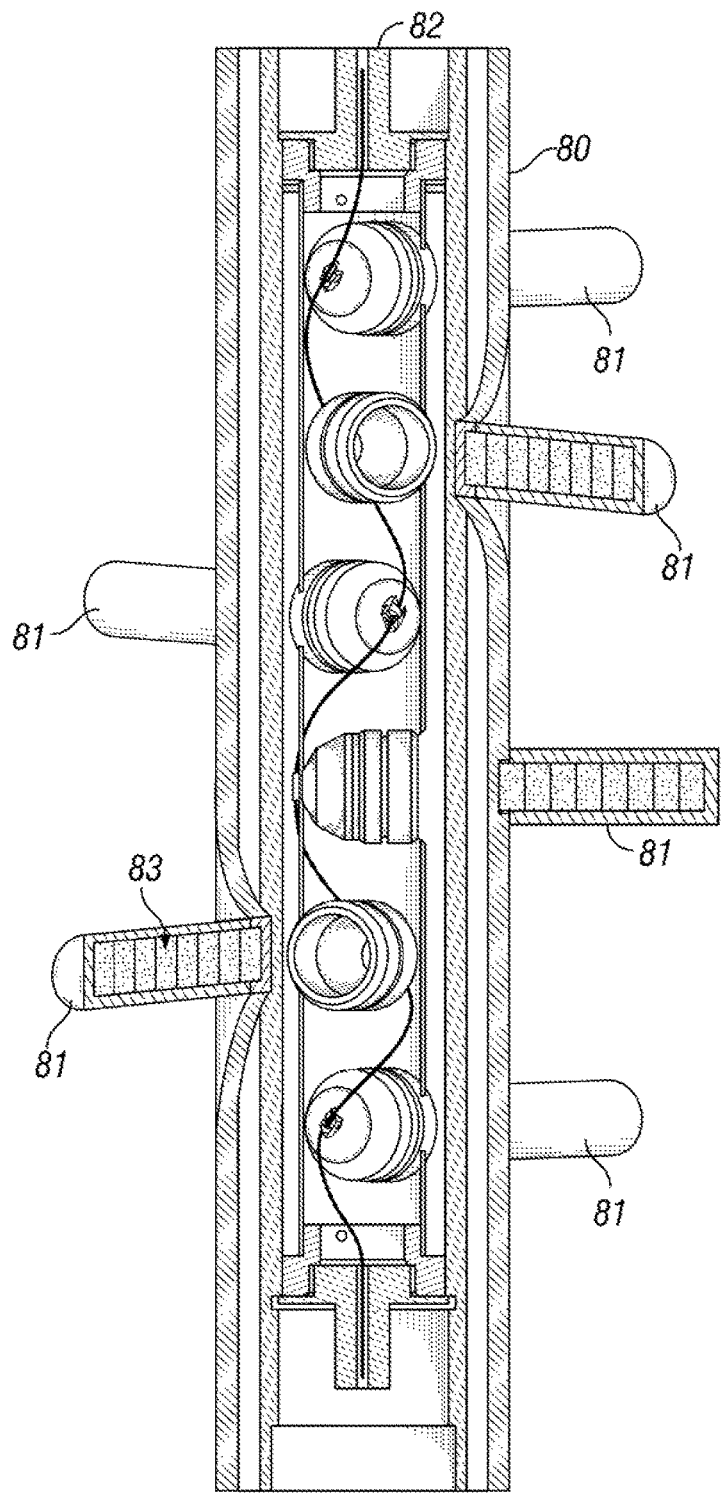
FIG. 5 is a perforating gun test setup.

Another test setup is illustrated in FIG. 5 wherein an existing perforating gun 82 is placed inside a piece of well casing 80 with test specimens 81 attached externally. In this example the test specimens 81 may be hollow to allow synthetic target segments 63 to be stacked inside. However, the test specimens 81 may also be a solid piece of metal or a solid synthetic target. The test specimens 81 may attach to the well casing 80 of the perforating gun 81. The attaching means may include threads, clips, interference fit, or some type of adhesive. Once the test specimens 81 are in place the perforating gun 82 fires, sending the explosive energy of each shaped charge through the well casing 80 and into each test specimen 81. This test setup allows for a full up gun system test.

Figure 6:
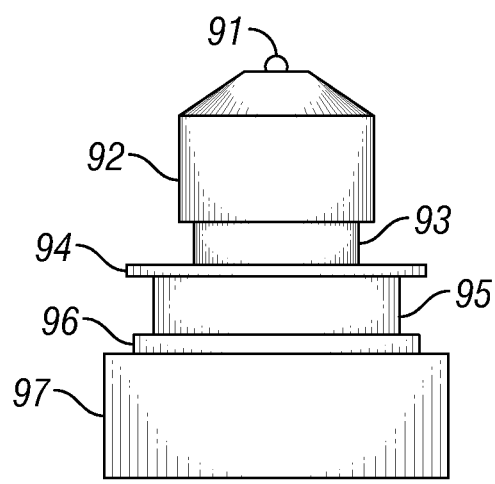
FIG. 6 is a shaped charge test setup.

Another test setup may include a shaped charge attached to a synthetic target as shown in FIG. 6. In this setup a detonating cord 91 is attached to a shaped charge 92. The shaped charge 92 is then flush with standoff 93. The standoff 93 may be a hollow cylinder spacer or a solid material. The standoff 93 may include a liquid, gas, or solid barrier for the shaped chare 92 to perforate. A scallop plate 94 is below the standoff. The scallop plate 94 simulates the outer casing of a perforating gun. A clearance means 95 is located below the scallop plate 94. The clearance means 95 may include a cylindrical or square device that may be hollowed and filled with water, gas or a solid material. The clearance means 95 simulates that distance inside a wellbore between the casing and the perforating gun. The wellbore is typically full of water, oil, drilling fluids, or some combination of fluids. The clearance means 95 may be filled with any fluid or combination of fluids that may exist in a wellbore. The casing of a wellbore is simulated using a steel plate 96. A synthetic target 97 is then located below the steel plate 96. The synthetic target 97, as disclosed herein, may be composed of a variety of materials at a variety of densities, porosities, or hardness.

In the test setup show in in FIG. 6 a shaped charge 92 is detonated by a detonating cord 91. The explosive blast of the shaped charge 92 will penetrate the standoff 93, the scallop plate 94, the clearance means 95, the steel plate 96, and the synthetic target 97. In this example only one synthetic is shown, however synthetic targets could be stacked in order to make a longer distance of material for the shaped charge 92 to penetrate. The entire setup may be fastened together using tape, adhesives, a mechanical device to hold the items 91-97 together, or some combination thereof.

Although the invention has been described in terms of particular embodiments which are set forth in detail, it should be understood that this is by illustration only and that the invention is not necessarily limited thereto. Alternative embodiments and operating techniques will become apparent to those of ordinary skill in the art in view of the present disclosure. Accordingly, modifications of the invention are contemplated which may be made without departing from the spirit of the claimed invention.

What is claimed is:

1. A shaped charge test apparatus comprising:
   a first end cap adapted to accept a shaped charge;
   a second end cap; and
   a body containing a hollow cylindrical interior holding a plurality of synthetic target discs, wherein the synthetic target discs are composed of sintered metallic powder.

2. The shaped charge test apparatus of claim 1 further comprising a first reservoir within the body contains a first fluid.

3. The shaped charge test apparatus of claim 1 further comprising a second reservoir within the first end cap containing a second fluid.

4. The shaped charge test apparatus of claim 3 wherein a shape charge is oriented to fire through the second fluid and the plurality of synthetic target discs.

5. The shaped charge test apparatus of claim 1 wherein the second end cap has a through opening.

* * * * *